US00PP36721P2

(12) United States Plant Patent
Hansen

(10) Patent No.: US PP36,721 P2
(45) Date of Patent: Jun. 3, 2025

(54) ***SPIGELIA* PLANT NAMED 'Orange Slices'**

(50) Latin Name: *Spigelia marilandica (L.)*
Varietal Denomination: Orange Slices

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,118

(22) Filed: Jul. 25, 2024

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson

(57) ABSTRACT

A unique cultivar of the *Spigelia* plant named 'Orange Slices' is characterized by vigorous, dense, upright, multi-stemmed, winter-hardy habit with dark-green, ovate to lanceolate leaves. Flowering begins in early June and continues for about four to five weeks, repeating again in the fall. Petals are orangish-red on the outside and light yellow on the inside. The new plant is especially suitable for a cut flower, for the landscape as a potted plant, and in the garden as a specimen or en masse.

3 Drawing Sheets

Botanical classification: *Spigelia marilandica* (L.).
Variety denomination: 'Orange Slices'.

STATEMENT REGARDING PRIOR DISCLOSURES UNDER 37 CFR 1.77(B)(6)

The new plant was first privately offered for sale on Jul. 25, 2023, and first sold on May 13, 2024, to Pleasant Run Nursery by Walters Gardens, Inc. No plants of *Spigelia* 'Orange Slices' have been sold or offered for sale anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Spigelia* plant known as *Spigelia* 'Orange Slices' and will be referred to hereafter by its cultivar name, 'Orange Slices', or the "new plant". *Spigelia* is in the Loganiaceae family. The new plant was a result of a self-pollination by the inventor at a wholesale perennial nursery in Zeeland, Michigan of the proprietary unreleased hybrid known only by the breeder code 12-5-4 (not patented). The new plant passed initial evaluation in the summer of 2017 and was assigned the breeder code 15-3-8 through the remaining evaluation process. 'Orange Slices' was first asexually propagated by shoot tip cutting in the spring of 2019 at the same nursery in Zeeland, Michigan. The unique characteristics of the new plant have been found to be reproducible and stable in successive generations of asexually propagated and the resultant plants are identical to the original selection.

BRIEF SUMMARY OF THE PLANT

*Spigelia* 'Orange Slices' is unique from all other *Spigelia* known to the inventor. The nearest comparison plants known to the inventor include: *Spigelia marilandica* 'Little Redhead' (not patented), *Spigelia marilandica* 'Ragin Cajun' (not patented) and 'Apple Slices' U.S. Plant patent application Ser. No. 18/445,736.

The parent has a flower that is not as deep an orange-colored and the foliage is not as dark green.

'Little Redhead' has a taller habit with lighter green foliage and the flowers are more reddish-colored. 'Ragin Cajun' has a slightly shorter and more rounded habit, the flower petals are lighter orangish-red on the outside and brighter yellow on the inside, and the foliage is lighter green. 'Apple Slices' has a more reddish on the outside of the flower and a slightly taller habit.

*Spigelia* 'Orange Slices' differs from all other *Spigelia* known to the inventor in the following repeatedly observed traits in combination:

1. Vigorous plants of dense upright habit, producing clean, dark-green, ovate to lanceolate leaves;
2. Multiple, densely-arranged, upright racemes;
3. Flower beginning in early June for about four to five weeks and repeating in the autumn;
4. Flowers of orangish-red on the outside with a light butter yellow on the inside;
5. Flower shape is gradually tapering funnelform with only slight flaring petal apices.

BRIEF DESCRIPTION OF THE DRAWINGS

The photographs of the new plant demonstrate the unique traits of *Spigelia* 'Orange Slices' and the overall appearance of a three-year-old plant growing in a full-sun garden in Zeeland, Michigan. The colors in the drawings are as accurate as reasonably possible with color reproductions. Variations in ambient light spectrum, source, and direction may cause the appearance of minor differences in color.

DETAILED BOTANICAL DESCRIPTION

Figure 1:
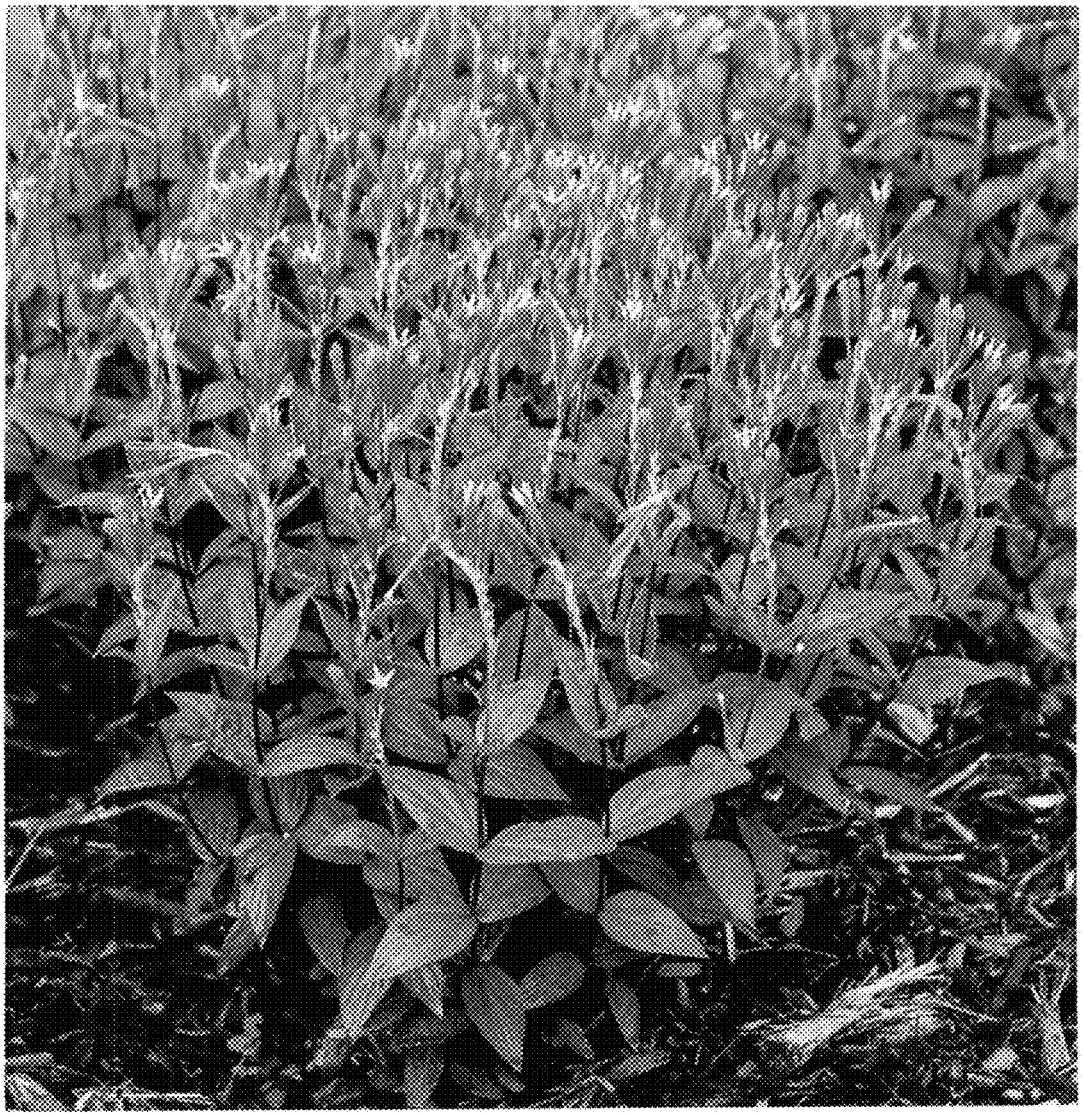
FIG. 1 shows a landscape habit view of the new plant in peak flower.
Figure 2:
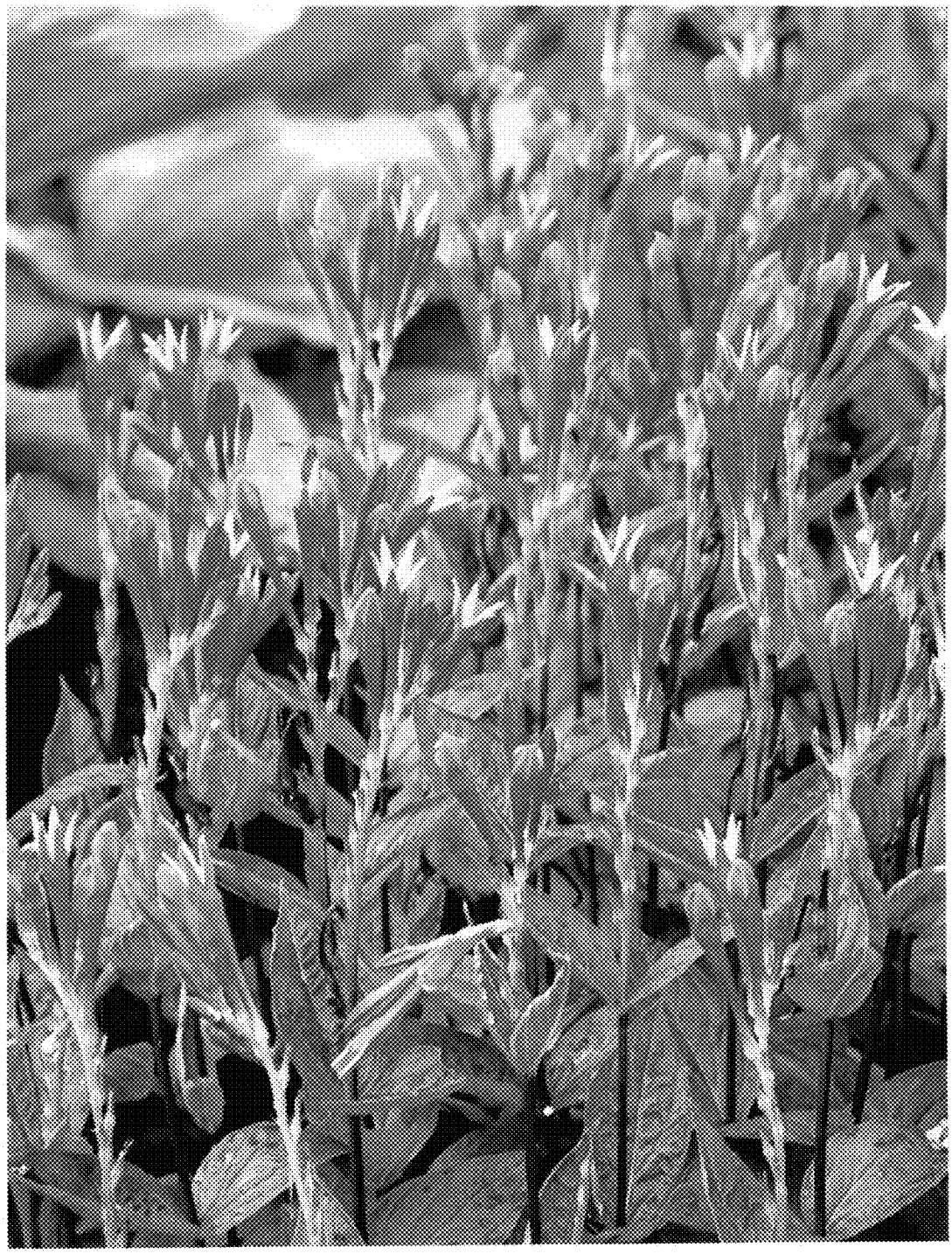
FIG. 2 shows a close-up of the flowers, buds, and foliage.
Figure 3:
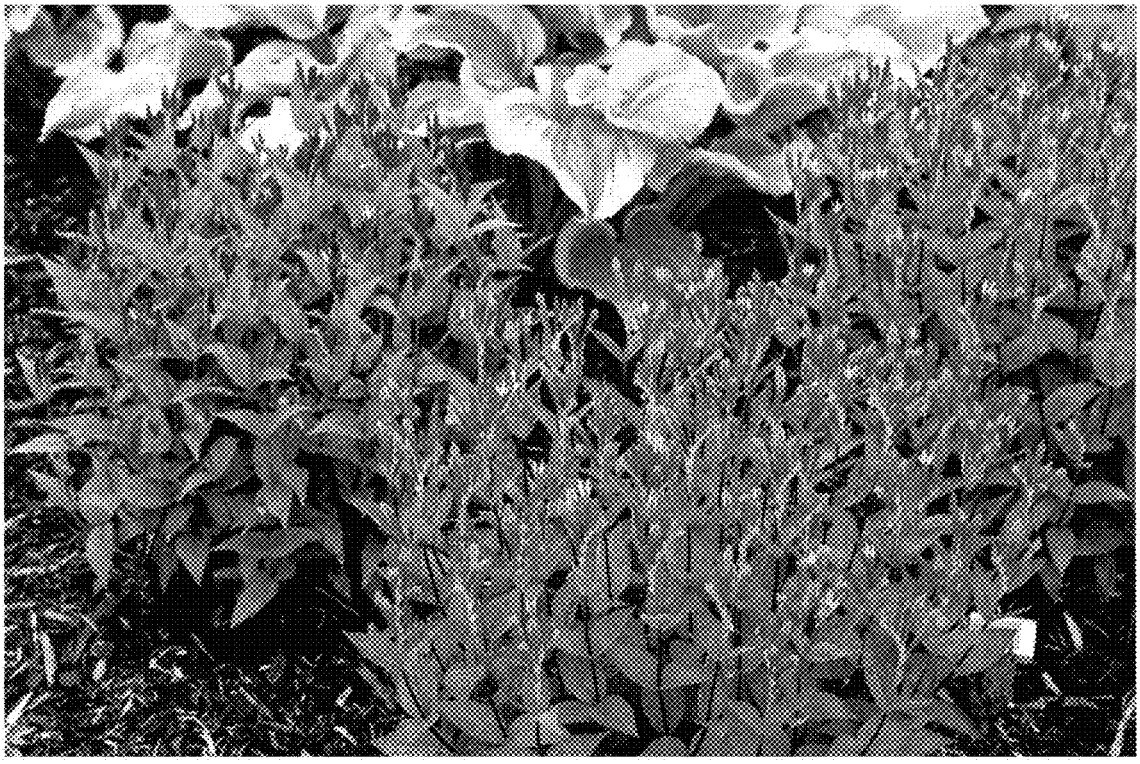
FIG. 3 shows two plants of 'Orange Slices' in the front center and back right, and a plant of 'Apple Slices' in the back left for comparison.

The following descriptions and color references are based on the 2015 edition of The Royal Horticultural Society Colour Chart except where common dictionary terms are used. *Spigelia* 'Orange Slices' has not been observed under all possible environments. The phenotype may vary slightly with different growing environments such as temperature, light, fertility, soil pH, moisture, and maturity levels, but without any change in the genotype. The following observations and size descriptions are based on four-year-old plants in a full-sun trial garden of a wholesale perennial nursery in Zeeland, Michigan with supplemental fertilizer and water as needed.

Botanical classification: *Spigelia marilandica;*

Parentage: Parent is the proprietary hybrid known by the breeder code 12-5-4;

Plant habit: Winter-hardy, evergreen herbaceous perennial; dense, producing about 150 stiff, upright stems; flowering to about 70 cm tall and 75 cm wide;

Propagation: Stem cuttings; rooting in about 3 weeks;

Time to produce finished crop in 3.8-liter pots: About 10 to 12 weeks; growth rate moderate;

Root: Fibrous and freely branching; to about 1 mm diameter; new root tip color creamy white nearest RHS NN155B, older roots pinkish-tan depending on soil type, nearest RHS N170D to RHS 174D;

Leaves: Simple; opposite; decussate; ovate to lanceolate; apex acute to narrowly acute; base truncate; sessile; margin entire; flat; micro-puberulent both adaxial and abaxial;

Leaf size: To about 89 mm long and 50 mm wide, average about 68 mm long and 35 mm wide;

Leaf color: Adaxial young expanding between RHS 138B and RHS 144A and abaxial young expanding between RHS 144A and RHS 143A; mature adaxial between RHS NN137A and RHS NN137B, mature abaxial between RHS 137B and RHS 147B; lacking anthocyanin expression;

Foliage fragrance: None detected;

Veins: Palmate; sunken adaxial and costate abaxial; puberulent to micro-puberulent adaxial and abaxial;

Vein color: Adaxial nearest RHS 146C, abaxial between RHS 145C and RHS 146D;

Petiole: Leaves sessile;

Stems: Cylindrical with fine ridges extending downwardly from the joint with leaf margins; stiff; upright; glabrous, limited branching below flowers; to about 62 cm long and 3.5 mm diameter at the base;

Stem color: Between RHS 147B and RHS 147C with little sun exposure, developing variable blush of nearest RHS N186C with high sun exposure;

Nodes: About 7 nodes before flowers; average internode spacing about 7.7 cm;

Node color: Between RHS 147B and RHS 147C with little sun exposure, developing variable blush of nearest RHS N186C with high sun exposure;

Inflorescence: Upright; flowering in about the upper 9 cm and about 5 cm wide; about 10 to 14 flowers per inflorescence;

Flowers: Perfect; complete; tubular; apex slightly flared to about 18 mm across at apex and 46 mm long; with fused corolla tube to about 40 mm long and 7 mm diameter below fusion; aspect upright;

Flower longevity: About 5 days on plant; self-cleaning;

Flower fragrance: None detected;

Flowering period: Beginning in early June and continuing for about four to five weeks, repeating in the autumn;

Buds one day prior to opening: Narrowly clavate with inflated distal bulb portion gradually narrowing to base; acute apex with rounded base; bulb portion carinate between petals; to about 43 mm long, 6 mm diameter in terminal bulb portion, basal tube portion to about 1.5 mm diameter;

Bud color: Proximally nearest RHS 46B, distally nearest RHS N45B, septa nearest RHS 45D;

Petals: Typically, five; lanceolate fused into corolla tube in the proximal 39 mm, free in the distal 11 mm; apex acute and only slightly flaring; margin entire; glabrous adaxial and abaxial;

Petal size: To about 50 mm long and 3.5 mm wide just above fusion;

Petal color: Adaxial face nearest RHS 11B, corolla tube between RHS 39C and RHS 39B; abaxial free portion between RHS 42A and RHS 42B, corolla tube between RHS 42A and RHS 42B, basal 2 mm adaxial and abaxial nearest RHS 145C;

Androecium: Typically, five;

*Filaments*.—Typically, five; cylindrical; glabrous; to about 36 mm long, adnate to inner corolla in proximal 31 mm and free in distal 5 mm, about 0.7 mm diameter; color free portion nearest RHS NN155B, proximal adnate portion nearest RHS 11C.

*Anther*.—Five; oblong elliptic; dorsifixed; longitudinal; introrse; about 3 mm long and 1 mm wide; color nearest RHS 2A.

*Pollen*.—Abundant; nearly microscopic; color nearest RHS 2A.

Gynoecium: One pistil per flower; to about 49 mm long;

*Style*.—Cylindrical; straight; about 37 mm long and 0.7 mm diameter; persistent after flower abscission; color nearest RHS 155D.

*Stigma*.—Oblong conical; puberulent; 7 mm long, about 0.7 mm diameter; color nearest RHS 150D.

*Ovary*.—Superior; ellipsoidal; glabrous; lustrous; about 2 mm long and 1.5 mm diameter; color nearest RHS 160B.

Calyx: Open, not fused; about 8 mm long and 3 mm across at apex;

Sepals: Five; linear; narrowly acute apex; base truncate, not fused; adaxial and abaxial slightly lustrous; margin entire; individually about 8 mm long and 1 mm wide at base;

Sepal color: Adaxial and abaxial nearest RHS 145D proximally and RHS 146B with a moderate blush of nearest RHS 175A distally;

Peduncle: Glabrous; stiff; upright; cylindrical; rarely branched; to 10 cm long and 2 mm diameter about distal leaves;

Peduncle color: Nearest RHS 145A with faint anthocyanin blush nearest RHS N186C in portions receiving high sun exposure;

Pedicle: Cylindrical; glabrous; upright; to 3 mm long and 1.5 mm diameter, decreasing to about 1 mm long distally;

Pedicle color: Nearest RHS 145C;

Fruit: Two-lobed capsule, circumscissile at base; to about 5.5 mm tall, 4 mm across and 7 mm wide; with persistent 5 mm long style portion; color at maturity nearest RHS N200A;

Seeds: One or two per ovary; spherical; asperous; to about 2 mm diameter; color nearest RHS N200A;

Hardiness and culture: The new plant grows best with full sun, light moisture and deep drainage; hardy to at least from USDA zone 5b through 9.

Disease and pest resistance: *Spigelia* 'Orange Slices' shows no susceptibility or resistance to pests or diseases other than that which is common to *Spigelia*.

I claim:

1. A new and distinct cultivar of *Spigelia* plant named 'Orange Slices', as herein described and illustrated.

* * * * *